United States Patent [19]
Crivello et al.

[11] Patent Number: 5,463,084
[45] Date of Patent: Oct. 31, 1995

[54] PHOTOCURABLE SILICONE OXETANES

[75] Inventors: James V. Crivello, Clifton Park, N.Y.; Hiroshi Sasaki, Nagoya, Japan

[73] Assignee: Rensselaer Polytechnic Institute, Troy, N.Y.

[21] Appl. No.: 11,892

[22] Filed: Feb. 1, 1993

Related U.S. Application Data

[63] Continuation-in-part of Ser. No. 837,473, Feb. 18, 1992, abandoned.

[51] Int. Cl.$^6$ .............. C07D 305/04; C07D 407/02; C08G 65/14; C08G 77/14
[52] U.S. Cl. .............. 549/214; 549/510; 549/511; 522/168; 522/172
[58] Field of Search .............. 549/60, 214, 472, 549/473, 510, 511, 168, 172; 522/168, 172

[56] References Cited

U.S. PATENT DOCUMENTS

| | | | |
|---|---|---|---|
| 3,673,216 | 6/1972 | Schroeter | 260/333 |
| 3,696,123 | 6/1972 | Schroeter et al. | 260/333 |
| 3,835,003 | 9/1974 | Schlesinger | 204/159.11 |
| 4,058,400 | 11/1977 | Crivello | 96/86 |
| 4,140,847 | 2/1979 | Orvik et al. | 528/403 |
| 4,394,403 | 7/1983 | Smith | 549/26 |

FOREIGN PATENT DOCUMENTS

| | | |
|---|---|---|
| 0043998 | 1/1982 | European Pat. Off. |
| 42-17502 | 9/1967 | Japan . |
| 49-020958 | 5/1974 | Japan . |
| 1021858 | 7/1974 | Japan . |
| 1561890 | 3/1980 | United Kingdom . |

OTHER PUBLICATIONS

CA 109(20):171011C "A Facile Synthesis of Oxetane Derivatives for Preparing Crosslinked Polyoxetane Resins Bearing the Bromide at the Spacer End", Motol et al, Bull. Chem. Soc. Japan, 61(5), 1653–9 (Eng) 1988.

CA 112:21367W "Polymer Reactions of the Pendant Alkyl Bromides of Soluble and Insoluble Polyoxetanes for the Preparation of Chemically Modified Polyethers", Motoi et al, Poly. J. (Tokyo) 1989, 21(6), 451–65 (Eng.)

CA 112:138302n "Use of Polyoxetane Resinssupported Quartemary Onium Salts as a Polymeric Phase–Transfer Catalyst for Preparing Ethers from Hydroxy Compounds and Alkyl Halides", Motoi et al, Bull. Chem. Soc. Jpn, 1989, 621(8), 2553–61 (Eng.).

CA 111:115840b "Oxetane Derivatives and their Polymers for Designing Functional Polymers Containing a Soft Somewhat Polar Polyether Network as a Polymer Support", Motoi et al, Bull. Chem. Soc. Jpn., 1989, 62(5), 1572–81 (Eng.).

Crivello and Lee, "New Epoxy Functional Silicone Monomers for Cationic UV Curing", Radtech, 90 North American Proceedings vol. 1, 432–445 (1990).

Eckberg et al. "Novel Photocurable Organosilicon Compositiions" Radtech, 90 North American Proceedings vol. 1, 358–370 (1990).

Primary Examiner—Susan W. Berman
Attorney, Agent, or Firm—Heslin & Rothenberg

[57] ABSTRACT

Novel 3-substituted oxetane monomers for photoinitiated cationic polymerization, compositions for polymerization containing these oxetanes, processes for polymerizing the monomers, and polymers produced thereby are disclosed.

A class of oxetane monomers have the formula

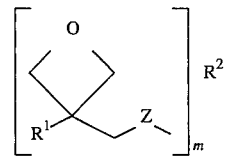

I wherein $R^1$ is hydrogen, alkyl of 1 to 6 carbons, fluorine, fluoroalkyl of 1 to 6 carbons, allyl, aryl, furan or thiophene; $R^2$ is a polyvalent radical chosen from the group consisting of linear or branched alkylene, linear or branched poly(alkyleneoxy), xylylene, and silicones; Z is oxygen or sulfur; and m is 2, 3 or 4.

7 Claims, No Drawings

PHOTOCURABLE SILICONE OXETANES

CROSS REFERENCE TO RELATED APPLICATION

This is a continuation-in-part of our U.S. application Ser. No. 07/837,473, filed Feb. 18, 1992, now abandoned.

BACKGROUND OF THE INVENTION

1. Field of the Invention

The invention relates to novel 3-substituted oxetane monomers for photoinitiated cationic polymerization, to compositions for polymerization, containing these oxetanes, to processes for polymerizing the monomers, and to polymers produced thereby.

2. Information Disclosure

Ultraviolet (UV)-induced polymerization, or curing, has become very important in the wood coating, metal decorating and printing industries as a consequence of its high cure and application speeds, essentially pollution-free operation, very low energy requirements and generally excellent properties. Early developments in this field centered about the photoinduced free radical polymerization of multifunctional acrylates and unsaturated polyesters. Today, these materials still remain the workhorses of the UV cure industry. While the bulk of the current research effort continues to be directed toward photoinduced free radical polymerizations, it is well recognized that ionic photopolymerizations also hold considerable promise in many application areas. Photoinduced cationic polymerizations are particularly attractive because of the wealth of different chemical and physical properties which can potentially be realized through the polymerization of a wide variety of monomers. Further, photoinitiated cationic polymerizations have the advantage that they are not inhibited by oxygen and thus, may be carried out in air without the need for blanketing with an inert atmosphere to achieve rapid and complete polymerization.

Until the present, photoinitiated cationic polymerization technology has centered about the photopolymerization of two types of monomers: epoxides and vinyl ethers. In particular, the photopolymerization of epoxides gives coatings with high thermal capability, excellent adhesion and good chemical resistance. Conventional photocurable epoxides have, however, the drawback that they undergo photopolymerization at rather slow rates. This factor renders them unsuited for certain applications such as paper and plastic coatings in which rapid UV curing is required.

Eckberg et al. [*Radtech '90 North American Proceedings* vol 1, 358–370 (1990)], which is incorporated herein by reference, discloses a series of linear and branched silicones having strained epoxide functional groups for photopolymerization. Catalysts and polymerization conditions are described.

Crivello and Lee [*Radtech '90 North American Conference Proceedings* Vol. 1, 432–445 (1990)], which is incorporated herein by reference, have described silicon-containing multifunctional monomers bearing strained cycloaliphatic epoxide rings that undergo especially rapid polymerization. These cationic photopolymerizations occur at speeds at least 100 times faster than the fastest commercial epoxide monomers. Similar silicon-containing monomers bearing open chain epoxides display rather poor UV curing responses.

Based on those observations, Crivello and Lee concluded that a major factor in the high photoresponse of the silicon-containing epoxides bearing cycloaliphatic epoxide rings is the high ring strain of the epoxide groups in these compounds. It is well known that epoxides have the highest ring strain of the cyclic ethers. Thus, all types of epoxides would be presumed to be more reactive in cationic UV photopolymerization than oxetanes, which would be more reactive than monomers containing five membered rings i.e.

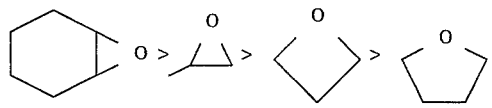

Further, it would also be expected that multifunctional oxetane monomers would be less reactive than the corresponding multifunctional epoxides. Oxetanes are known to undergo polymerization but their rates of polymerization are not discussed in the art in which the oxetanes are disclosed.

U.S. Pat. No. 4,058,400 (Crivello) discloses that 3,3-bischloromethyloxetane and alkoxyoxetanes may be cationically photopolymerized.

U.S. Pat. No. 3,673,216 (Schroeter) discloses a series of 4,4-dialkyl-2-alkoxyoxetanes and states that they may be polymerized with Friedel-Crafts catalysts.

German Patent 1,021,858 (Bodenbenner and Wegler) discloses oxetanes of general formula

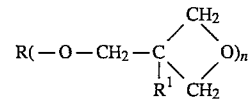

wherein R is an aromatic residue having two or more valences and $R^1$ is ethyl. Specifically disclosed are compounds wherein R is

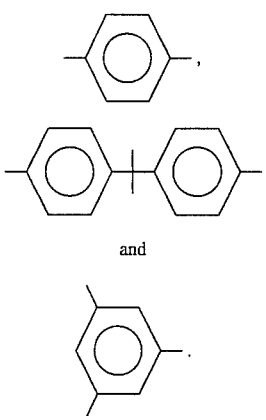

and

SUMMARY OF THE INVENTION

It is an object of the invention to provide monomers that can be polymerized with short UV exposure times.

It is a further object of the invention to provide monomers that can be polymerized without the need to exclude oxygen.

It is a further object of the invention to provide monomers that may be easily prepared from readily available starting materials.

It is a further object of the invention to provide polymers that are strong, chemically resistant, and adherent.

It has been surprisingly found that a number of di-and trifunctional oxetane monomers show exceptionally high reactivity in cationic UV curing. Their reactivity is approximately the same as those monomers containing strained epoxide groups, which would not have been predicted based on the current state of knowledge of cationic UV curing.

The oxetane monomers of this invention have the additional advantage that they may be prepared in high yields by straightforward synthetic methods which do not employ epoxidation. In contrast, the multifunctional cycloaliphatic epoxide monomers presently in use are commonly prepared by epoxidation of the corresponding olefin, a process that is usually inconvenient and costly and sometimes dangerous. For these reasons, cycloaliphatic epoxide resins are considered a specialty business.

In one aspect the invention relates to a series of 3-substituted oxetanes of formula

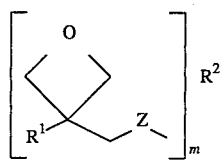

I wherein $R^1$ is hydrogen, alkyl of 1 to 6 carbons, fluorine, fluoroalkyl of 1 to 6 carbons, allyl, aryl, furan or thiophene;

$R^2$ is a polyvalent radical chosen from the group consisting of linear or branched alkylene, linear or branched poly(alkyleneoxy),

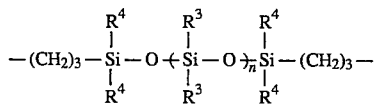

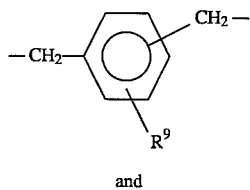

and

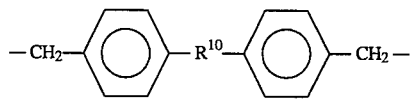

$R^3$ is chosen from the group consisting of alkyl of 1–4 carbons and

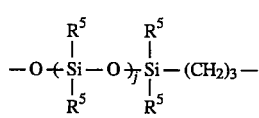

$R^4$ is alkyl of 1 to 4 carbons;
$R^5$ is alkyl of 1 to 4 carbons;

$R^9$ is hydrogen, alkyl of 1 to 4 carbons, alkoxy of 1 to 4 carbons, halogen, nitro, cyano, mercapto, lower-alkyl carboxylate, COOH or $CONH_2$;

$R^{10}$ is O, S, $CH_2$, NH, SO, $SO_2$, $C(CF_3)_2$ or $C(CH_3)_2$;

Z is oxygen or sulfur;

j is zero or an integer from 1 to 100;

m is 2, 3 or 4; and n is an integer from zero to 2000.

Preferably $R^1$ is lower-alkyl, most preferably ethyl. $R^4$ and $R^5$ are preferably methyl. Z is preferably oxygen. For polymers of high surface hardness, n is preferably zero to six; for polymers of high tensile strength, n is preferably 100 to 200; $R^9$ is preferably hydrogen and $R^{10}$ is preferably O, $CH_2$, $C(CF_3)_2$ or $C(CH_3)_2$. Throughout the specification and claims variables are defined when introduced and retain that definition thereafter.

Another preferred embodiment includes compounds of the formula

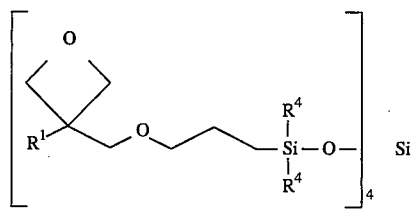

VI

The compounds of formula VI may be thought of as compounds of formula I wherein

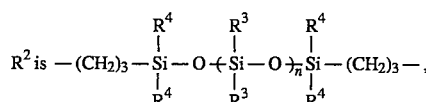

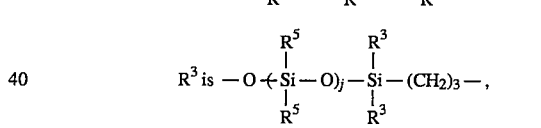

n is one, j is zero, m is four and Z is oxygen. In general, branched silicones having multiple appended oxetanes are formed (i.e. m is 3 or 4) when $R^3$ is a siloxane, whereas linear bis(oxetanyl)silicones are formed when $R^3$ is lower alkyl.

In another aspect the invention relates to oxetanes of the formula:

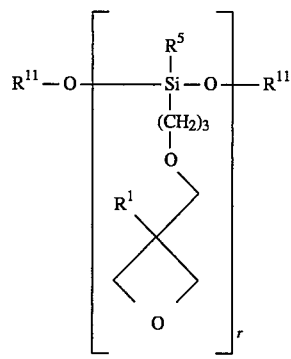

wherein r is an integer from 25 to 200; and $R^{11}$ is alkyl of 1 to 4 carbons or trialkylsilyl.

In another aspect, the invention relates to UV-curable compositions comprising the foregoing monomers and cationic photoinitiators. In addition to the foregoing monomers, the UV-curable compositions may comprise oxetane monomers IV and V

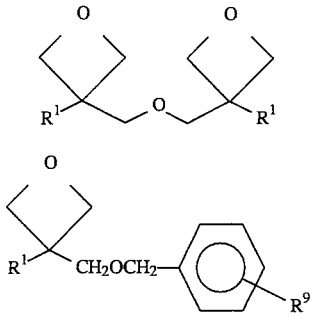

IV

V particularly those in which $R^9$ is hydrogen, halogen or alkoxy. Preferred photoinitiators are triarylsulfonium salts and diaryliodonium salts.

In another aspect, the invention relates to processes for preparing crosslinked propyloxy polymers comprising (a) mixing an oxetane monomer of the invention with a cationic photoinitiator and (b) exposing the mixture to ultraviolet light.

In another aspect, the invention relates to crosslinked propyloxy polymers produced by polymerization of the monomers of the invention. In the case where m in formula I is two, polymeric products may be represented by the formula:

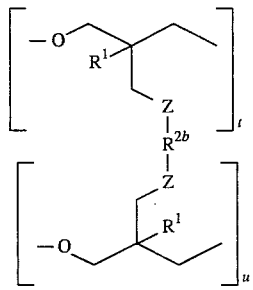

wherein $R^{2b}$ is the same as $R^2$ and additionally may be

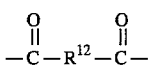

and t and u are numbers from 2 to 2000.

In the case where m is four, (i.e. those arising from monomers such as VI) polymeric products are represented by the formula:

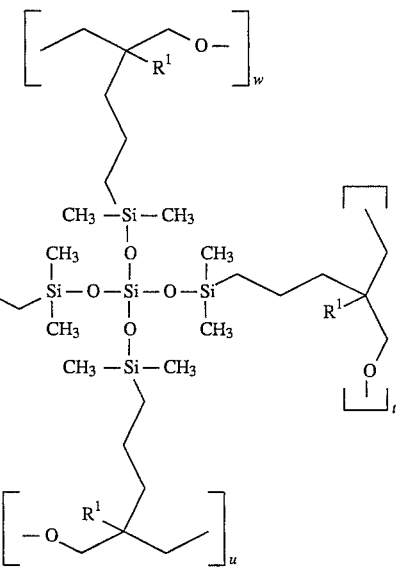

where v and w are also numbers from 2 to 2000.

In the case where the monomer has the structure of formula IV, polymeric products are represented by the formula:

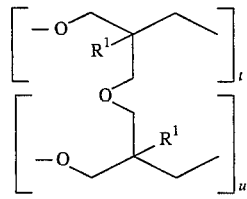

DETAILED DESCRIPTION INCLUSIVE OF PREFERRED EMBODIMENTS

The oxetanes of the invention may be synthesized by the procedure of Pattison [*J. Am. Chem. Soc.* 1957, 79] from 1,3 diols:

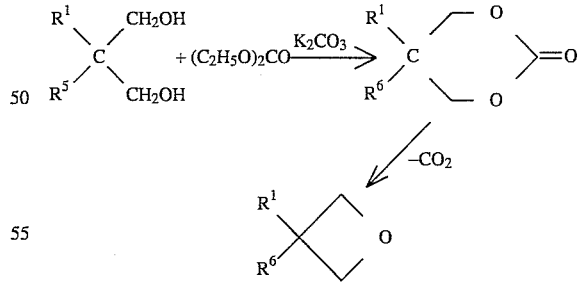

The 1,3-diols are available by aldol condensation and crossed Cannizzaro reaction of formaldehyde and carbonyl compounds by procedures well-known in the art:

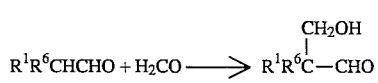

-continued

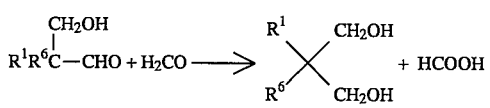

The compounds wherein $R^6$ is $CH_2OH$ are of particular utility for the synthesis of monomers of the invention:

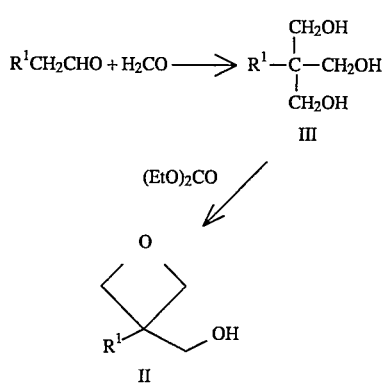

When it is desired that Z be sulfur, the free hydroxyl may be converted to a mercaptan by procedures well known in the art. The triol III wherein $R^1$ is ethyl, trimethylolpropane, is commercially available and the resulting oxetane II was used in the syntheses that follow. Difunctional oxetane monomers containing ether groups may be synthesized utilizing the following chemistry:

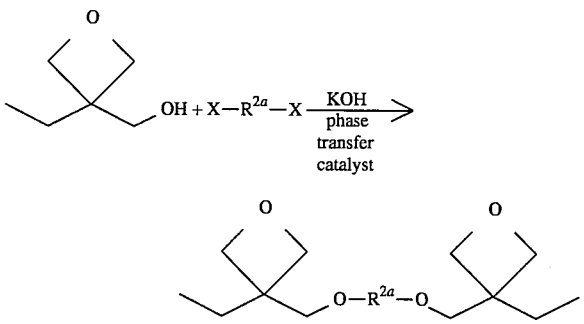

In the above equation $R^{2a}$ may be alkylene, xylylene, poly(alkyleneoxy), or

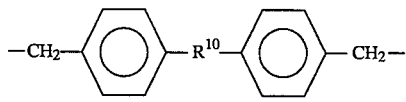

X is bromine, chlorine or iodine.

Compounds of formula I in which m is three or four may be made analogously to the compounds shown above wherein m is two. Thus, for example, when $R^{2a}$ is a branched or straight alkylene chain containing three or four replaceable groups X, compounds of the appropriate formulas I are synthesized.

In a similar fashion, monofunctional benzylether oxetanes (formula V) can be prepared from 3-hydroxymethyloxetanes. These monofunctional oxetanes are useful as reactive diluents, which may be used to reduce the viscosity and improve the reactivity of multifunctional oxetanes or epoxides in cationic photopolymerization compositions.

Monomers containing ester groups may be prepared using an ester exchange reaction:

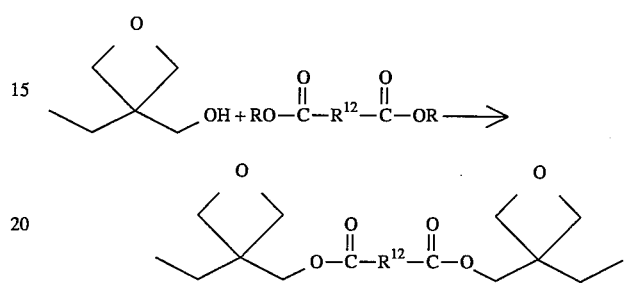

and are described in U.S. Pat. No. 3,278,554.

Silicon-containing oxetane monomers are synthesized by the generalized reaction sequence shown:

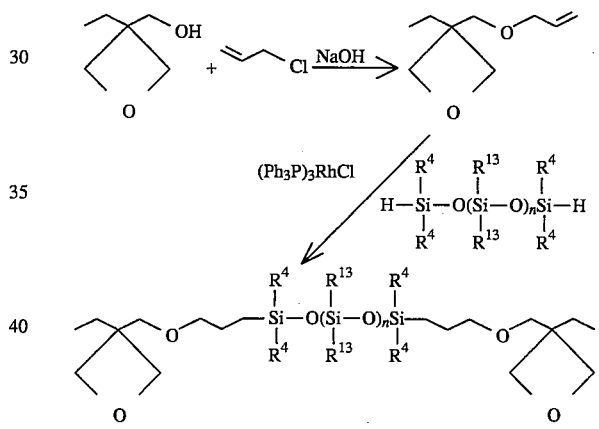

wherein $R^{13}$ is alkyl of 1 to 4 carbons or

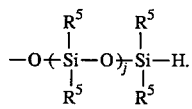

When $R^{13}$ contains additional SiH bonds, additional oxetane residues will be added.

In the case where it is desired that Z be sulfur, the oxetane II may be tosylated and reacted with allyl sulfide.

Multifunctional oxetane monomers can be photopolymerized using a wide variety of cationic photoinitiators. Prominent among such monomers are diaryliodonium salts, triarylsulfonium salts and ferrocenium salts. Typical, very useful photoinitiators are shown below in which $R^7$ and $R^8$ are alkyl chains of varying lengths from 1 to 18 carbon atoms, M is a metal, typically antimony, and X is halogen.

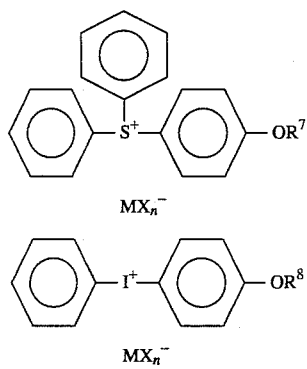

The above photoinitiators can be used in concentrations of from 0.1 to 20 weight percent based on the multifunctional oxetane monomer. In addition to photoinitiators, photosensitizers may also be added to adjust the wavelength of sensitivity throughout the visible and UV regions of the electromagnetic spectrum. Typical sensitizers which may be used in the course of this invention are listed in Crivello *Adv. in Polymer Sci.* 62, 1 (1984), which is incorporated herein by reference. Examples include pyrene, perylene, acridine orange, thioxanthone, 2-chlorothioxanthone, and benzoflavin.

The rapidly curable compositions of this invention may be exposed to irradiation from a wide variety of sources, e.g. mercury arc lamps, xenon arc lamps, fluorescent lamps, carbon arc lamps, tungsten-halogen reprographic lamps and ambient sunlight. The lamps can include envelopes capable of transmitting light of a wave length from about 1848Å to 4000Å and preferably 2400Å to about 4000Å. The lamp envelope can consist of quartz or of Pyrex. When using UV lamps, the irradiation flux on the substrate is preferably at least 0.01 Watt per square inch to effect cure of the organic resin within 1 to 20 seconds and to permit the cure to be carried on continuously, as for example in a paper or metal coating line.

The curable compositions of this invention may contain inactive ingredients such as inorganic fillers, dyes, pigments, extenders, viscosity control agents, process agents, and UV screens in amounts of up to 100 parts filler per 100 parts oxetane monomer. The curable compositions may be applied to such substrates as metal, rubber, plastic, molded parts or films, paper, wood, glass cloth, concrete and ceramics.

Some of the applications in which the curable compositions of the present invention can be used are, for example, protective, decorative and insulating coatings, potting compounds, printing inks, sealants, adhesives, photoresists, wire insulation, textile coatings, laminates, impregnated tapes and printing plates.

The following examples are given by way of illustration and not by way of limitation.

Synthesis of Precursors

EXAMPLE 1

3-Ethyl-3-hydroxymethyloxetane

Into a 150 mL round bottom flask fitted with a magnetic stirrer, thermometer, condenser, distillation head and receiver were placed a mixture of 67.0 g (0.5 mol) trimethylolpropane, 59.0 g (0.5 mol) of diethyl carbonate and 0.05 g of potassium hydroxide dissolved in 2 mL of absolute alcohol. The mixture was refluxed until the pot temperature was below 105° C. and then distilled keeping the head temperature at 76°–78° C. Distillation was continued until the pot temperature was 145° C. Then, the pressure was reduced gradually to 15 mm Hg maintaining the pot temperature at 140°–150° C. Upon heating above 180° C., carbon dioxide evolution was rapid and most of the product distilled at 100°–160° C. Redistillation through an efficient column gave 43.9 g of 3-ethyl-3-hydroxymethyloxetane (yield: 76%, b.p.:114°–115° C. at 16 mm Hg).

EXAMPLE 2

3-Ethyl-3-allyloxymethyloxetane

To a solution of 23.2 g (0.2 mol) of 3-ethyl-3-hydroxymethyloxetane in 48.4 g (0.4 mol) of allylbromide and 50 g of a 50 wt % aqueous solution of potassium hydroxide in a 300 mL round bottom flask equipped with a magnetic stirrer was added 1.0 g of tetra-n-butylammonium bromide with vigorous stirring at 0° C. After 24 hrs, 100 mL of dichlorometane and 100 mL of water were added to the reaction mixture. The organic phase was washed with water twice, dried over magnesium sulfate, filtered and the solvent removed on a rotary evaporator. The residue was purified by distillation under vacuum, giving 28.6 g of 3-ethyl-3-allyloxymethyloxetane (yield 92%, b.p.:55° C. at 1.5 mm Hg).

EXAMPLE 3

2-(3-Oxetane)butyl tosylate

A solution of p-toluenesulfonyl chloride (91.2 g; 0.48 mol) in dry pyridine (150ml) was added to 3-ethyl-3-hydroxymethyloxetane (27.8 g; 0.24 mol) in dry pyridine (100 ml) with cooling in an ice/salt bath. When the first exothermic stage of reaction was over, the mixture was shaken overnight at room temperature, poured onto ice/water (500 ml), and extracted with methylene chloride. The extracts were washed with ice-cold and diluted HCl, NaHCO$_3$ solution, and water and dried over MgSO$_4$. After removal of the solvent the ester was obtained as a light reddish-brown oil, which is pure enough for most purposes. Yield: 55.7 g (86%).

EXAMPLE 4

3-Ethyl-3-allylthiomethyloxetane

A solution of 2-(3-oxetane)butyl tosylate of example 3 in an inert solvent such as THF is stirred with one equivalent of allyl mercaptan at room temperature until reaction is complete. The solvent is stripped and the residue taken up in ether. The ether is washed with saturated aqueous NaHCO$_3$, dried over MgSO$_4$ and stripped to provide 3-ethyl-3-allythiomethyloxetane.

Synthesis of Monomers

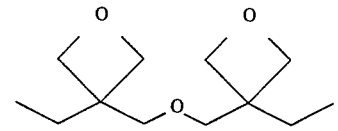

Monomer 1 (formula IV; $R^1$=ethyl)

Employing the procedure of example 1, a mixture of 25.0 g (0.1 mol) of ditrimethylolpropane, 23.6 g (0.2 mol) of diethylcarbonate and 5.0 g of potassium carbonate was refluxed until the pot temperature was below 120° C. The mixture was distilled keeping the head temperature 76°–78° C. Distillation was continued until the pot temperature was 180° C., and then the mixture became viscous as a polymer formed. Upon heating above 220° C., the viscous polymer melt reverted to a mobile liquid and carbon dioxide evolution was rapid. Then the pressure was reduced gradually to 15 mm Hg, and most of the material distilled at 120°–170° C. Redistillation through an efficient column gave 8.9 g of monomer 1 (yield: 42%, b.p.: 165°–170° C at 16 mm Hg).

TABLE 1

Difunctional Monomers

| Monomer # | $R^{2c}$ |
|---|---|
| 2 | $-(CH_2)_4-$ |
| 3 | $-(CH_2)_{12}-$ |
| 4 | $-C(=O)-CH_2-CH_2C(=O)-$ |
| 5 | $-(CH_2)_3-Si(CH_3)_2-O-Si(CH_3)_2-(CH_2)_3-$ |
| 6 | $-(CH_2)_3-[Si(CH_3)_2-O]_2-Si(CH_3)_2-(CH_2)_3-$ |
| 7 | $-(CH_2)_3-[Si(CH_3)_2-O]_3-Si(CH_3)_2-(CH_2)_3-$ |
| 14 | $-CH_2-C_6H_4-CH_2-$ (para) |
| 15 | $-CH_2-C_6H_4-CH_2-$ (meta) |
| 16 | $-CH_2-C_6H_4-CH_2-$ (ortho) |

Monomer 2

To a solution of 34.8 g (0.3 mol) of 3-3-ethylhydroxymethyloxetane in 21.6 g (0.1 mol) of 1,4-dibromobutane and 50 g of a 50 wt % aqueous solution of potassium hydroxide was added 1.0 g of tetra-n-butylammonium bromide with vigorous stirring at 0° C. After 24 hrs, 100 mL of ether and 100 mL of water were added to the reaction mixture. The organic phase was washed with water twice, dried over magnesium sulfate, filtered and evaporated. The residue was purified by flash column chromatography on silica gel with ethyl acetate/hexane (volume ratio 1:1), giving 19.8 g of monomer 2. (yield:69%)

Monomer 3

The procedure for monomer 2 was repeated using 3-ethyl-3-hydroxymethyloxetane (12.8 g; 0.11 mol) and 1,12-dibromododecane (16.4 g; 0.05 mol). A colorless oil was obtained on purification by flash column chromatography on silica gel with ethyl acetate/hexane (volume ratio 1:4) yield: 8.2 g (48%).

Monomer 4

A mixture of 25.6 g (0.22 mol) of 3-ethyl-3-hydroxymethyloxetane, 14.6 g (0.1 mol) of dimethylsuccinate and 0.8 g of titanium tetraethoxide was distilled keeping the head temperature under 70° C. Distillation was continued until the pot temperature was 150° C., and then the pressure was reduced gradually to 15 mm Hg. The resulting carbonate was purified by flash column chromatography on silica gel with ethyl acetate/hexane (volume ratio 9:1), giving 27.1 g of monomer 4 (yield:86%).

Monomer 5

A mixture of 9.4 g (0.06 mol) of 3-ethyl-3-allyloxymethyloxetane, 3.4 g (0.025 mol) of 1,1,3,3-tetramethyldisiloxane and 0.01 g of tris(triphenylphosphine)rhodium(I) chloride in toluene(15 mL) was stirred overnight at 80° C. The toluene was removed with the aid of a rotary evaporator. The residue was purified by flash column chromatography on silica gel with ethyl acetate/hexane (volume ratio 1:4), giving 7.5 g of monomer 5 (yield:67%).

Monomer 6

The procedure for monomer 5 was repeated using 9.4 g (0.06 mol) of 3-ethyl-allyloxymethyloxetane, 5.2 g (0.025 mol) of 1,1,3,3,5,5-tetramethylldisiloxane, and 0.01 g of tris(triphenylphosphine)rhodium(I) chloride in toluene (15 mL). A colorless oil (monomer 6) was obtained on purification by flash column chromatography on silica gel with ethyl acetate/hexane (volume ratio 1:4) in a yield of 8.3 g (64%).

Monomer 7

The procedure for monomer 5 was followed using 9.4 g (0.06 mol) of 3-ethyl-3-allyloxymethyloxetane, 7.0 g (0.025 mol) of 1,1,2,2,3,3,7,7-octamethyltetrasiloxane, and 0.01 g of tris(triphenylphosphine)rhodium(I) chloride in toluene (15 mL). A colorless oil (monomer 7) was obtained on purification by flash column chromatography on silica gel with ethyl acetate/hexane (volume ratio 1:4) in a yield of 8.2 g (55%).

Monomer 14

The procedure for monomer 3 was repeated using 3-ethyl-3-hydroxymethyloxetane (12.8 g; 0.11 mol) and α,α'-dibromo-p-xylene (13.2 g; 0.05 mol). A colorless oil was obtained on purification by flash chromatography on silica gel with ethyl acetate/hexane (2:3); yield: 15.4 g (92%).

Monomer 15

The procedure for monomer 3 was repeated using 3-ethyl-3-hydroxymethyloxetane (12.8 g; 0.11 mol) and α,α'-dibromo-m-xylene (13.2 g; 0.05 mol). A colorless oil was obtained on purification by flash chromatography on silica gel with ethyl acetate/hexane (2:3); yield: 15.3 g (90%).

Monomer 16

The procedure for monomer 3 was repeated using 3-ethyl-3-hydroxymethyloxetane (12.8 g; 0.11 mol) and α,α'-dibromo-o-xylene (13.2 g; 0.05 mol). A colorless oil was obtained on purification by flash chromatography on silica gel with ethyl acetate/hexane (2:3); yield: 15.3 g (90%).

TABLE 2

Polyfunctional Monomers

| Monomer # | Structure |
| --- | --- |
| 8 | 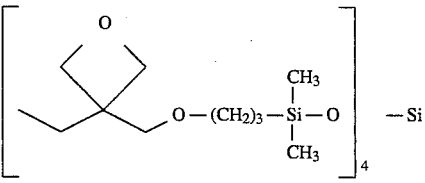 |
| 9 | 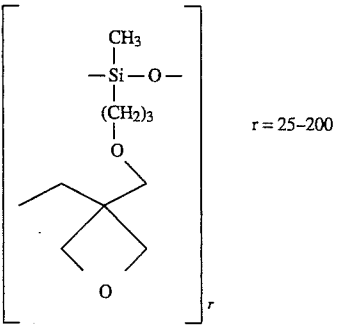 |

Monomer 8

The procedure for monomer 5 was followed using 7.9 g (0.05 mol) of 3-ethyl-3-allyloxymethyloxetane, 3.3 g (0.01 mol) of tetrakisdimethylsilyloxysilane, and 0.01 g of tris-(triphenylphosphine)rhodium(I) chloride in 15 mL toluene. Monomer 8 was obtained in 7.8 g (80% yield) as a colorless oil on purification by flash column chromatography on silica gel with ethyl acetate/hexane (volume ratio 1:3).

Monomer 9

The procedure for monomer 5 was followed using 7.9 g (0.05 mol) of 3-ethyl-3-allyloxymethyloxetane, 2.4 g (0.04 mol eq.) of poly(methylhydrogensiloxane) (GE 554300C, General Electric Co.), and 0.01 g of tris (triphenylphosphine)rhodium(I) chloride in 15 mL toluene. An oligomeric product (monomer 9) was obtained as a brown oil in 94% (8.1 g) yield on removal of the toluene on a rotary evaporator.

Monomers 10–13

By a procedure analogous to that for monomers 5 through 8, it is contemplated that 3-ethyl-3-allylthiomethyloxetane of example 4 may be converted to the sulfur analogs of monomers 5 through 8.

TABLE 3

Monofunctional Monomers

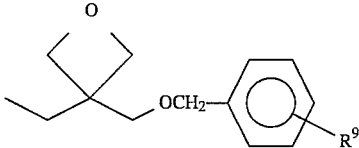

| Monomer # | R⁹ |
| --- | --- |
| 17 | H |
| 18 | 4-F |
| 19 | 4-OCH₃ |

Monomer 17

The procedure for monomer 2 was followed using 34.1 g (0.2 mol) of benzyl bromide and 11.6 g (0.1 mol) of 3-ethyl-3-hydroxymethyloxetane. A colorless oil was obtained in 68% yield by flash chromatography on silica gel with ethyl acetate/hexane; 3:7.

Monomer 18

The procedure for monomer 17 was followed using 37.8 g (0.2 mol) of 4-fluorobenzyl bromide. A colorless oil was obtained from flash chromatography on silica gel with ethyl acetate/hexane (3:7); yield: 18.2 g (92%).

Monomer 19

The procedure for monomer 17 was followed using 37.0 g (0.2 mol) of p-methoxybenzyl bromide. Monomer 19 was obtained in 76% yield.

Photopolymerization of Monomers 1–9

Photopolymerizations of the monomers were carried out using neat monomers containing various concentrations of the onium salts shown below as photoinitiators.

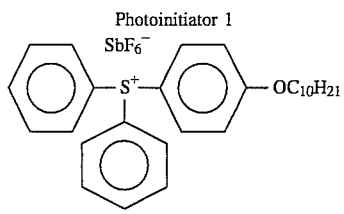

Photoinitiator 1

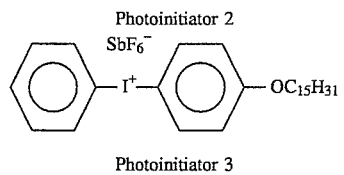

Photoinitiator 2

Photoinitiator 3

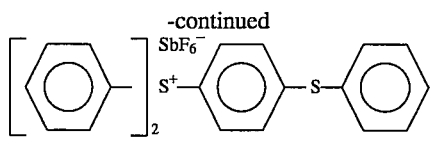

In addition, three epoxide resins with structures shown below were evaluated using the same photoinitiators in side-by-side comparisons. Silicone epoxide 1 has been reported to be very reactive in cationic UV cure; epoxide 2 is considered a "high reactivity" biscycloaliphatic epoxide which is available commercially; epoxide 3 is a simple epoxide lacking the additional strain of a fused ring and may be considered the 3-membered ring analog of the oxetanes of the invention.

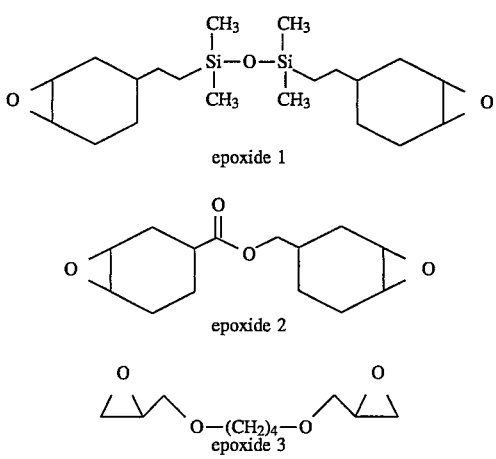

The rates of polymerization of the various monomers were measured by recording their gel times in 10 μL capillary tubes using a "GEL POINTE" apparatus. This apparatus is equipped with a tungsten-halogen lamp and the time from when the lamp is turned on until the oscillation of the meniscus ceases in the capillary tube is recorded as the gel time. The shorter the gel time, the more reactive the monomer is in cationic UV curing.

In addition, the tack free energies (T.F.E.) of the various multifunctional oxetane monomers were measured and compared with one another and with the above epoxide reference resins. A conveyor-type UV radiation apparatus (Fusion Systems, F-300 Laboratory UV Cure Processor) was used for these studies. The minimum energies in millijoules per square centimeter ($mJ/cm^2$) were recorded. Thus, the lower the energy required to cure a monomer, the higher its reactivity.

The results of polymerization studies are shown in Table 4. The photoinitiator concentration was 0.25 mol % per reactive functional group; the lamp intensity was 300 w/cm$^2$ at 16.5 cm; and the film thickness was 75 μm.

TABLE 4

Gel Times and Tack Free Energies of UV Cured Multifunctional Oxetanes

| Monomer | Photoinitiator | Gel Time (sec.) | T.F.E. ($mJ/cm^2$) |
|---|---|---|---|
| 1 | 1 | 370 | 450 |
| 2 | 1 | 320 | 500 |
| 3 | 1 | 110 | 550 |

TABLE 4-continued

Gel Times and Tack Free Energies of UV Cured Multifunctional Oxetanes

| Monomer | Photoinitiator | Gel Time (sec.) | T.F.E. ($mJ/cm^2$) |
|---|---|---|---|
| 4 | 1 | >500 | >1000 |
| 5 | 1 | 200 | 550 |
| 6 | 1 | 230 | 650 |
| 7 | 1 | 250 | 700 |
| 8 | 1 | 30 | 500 |
| 9 | 1 | * | * |
| Epoxide 1 | 1 | 60 | <80 |
| Epoxide 2 | 1 | >500 | 4500 |
| 1 | 2 | 210 | 550 |
| 2 | 2 | 175 | 550 |
| 3 | 2 | 55 | 550 |
| 4 | 2 | >500 | >1000 |
| 5 | 2 | 65 | 550 |
| 6 | 2 | 90 | 650 |
| 7 | 2 | 120 | 700 |
| 8 | 2 | 10 | 500 |
| 9 | 2 | * | * |
| Epoxide 1 | 2 | 5 | >80 |
| Epoxide 2 | 2 | >500 | >4000 |

*Photoinitiators were insoluble in the monomer.

A comparison of the gel time data in Table 4 shows that surprisingly, certain of the multifunctional oxetane monomers of this invention undergo more rapid UV cure than the "highly reactive" epoxide monomers used as references. For example, using photoinitiator 1, oxetane monomer 8 is more reactive than epoxide 1. At the same time, virtually all of the oxetane monomers with the exception of monomer 4 are more reactive than epoxide 2. This same pattern of gel time measurements is shown with photoinitiator 2. The tack free time measurements show the same trends. With photoinitiators 1 and 2 respectively, tack free energies of <80 and >80 $mJ/cm^2$ for the silicone-epoxide 1 were recorded while 4500 and 4000 $mJ/cm^2$ was found for epoxide 2. Again, surprisingly, the multifunctional oxetane monomers are more reactive on this basis than the "high reactivity" biscycloaliphatic epoxide 2.

Side-by-side comparison of the multifunctional oxetane monomers with the most reactive epoxide monomers known to the inventors clearly shows the unexpected reactivity of the UV curable oxetane compositions of this invention.

A similar set of polymerization studies is shown in Table 5. In this case the monomers 14, 15 and 16 were compared to epoxides 2 and 3 and to oxetane monomer 2. The polymerizations were carried out as before except that the films were 10 μm thick and the photoinitiator was photoinitiator 3.

TABLE 5

| Monomer # | gel time (in seconds) | tack free energy ($mJ/cm^2$) |
|---|---|---|
| 14 | 5 | 350 |
| 15 |  | 400 |
| 16 |  | 400 |
| 2 | 60 | 600 |
| epoxide 3 | 75* | 2500 |
| epoxide 2 | ** | 1300 |

*epoxide 3 remained a liquid for the duration of the exposure
**the viscosity of the monomer was too high to measure a gel time The rates of polymerization of monofunctional 3-benzyloxymethyloxetanes 17, 18 and 19 were measured by following the rate of disappearance of the oxetane band at 980 cm$^{-1}$ in the infrared. In order to determine the effect of the benzyl group on the rates of photopolymerization, the study included monomer 2 which does not contain a benzyl group. The irradiation doses required to reach various conversions were determined and the results are presented in Table 6. The photoinitiator was photoinitiator 3 at 0.5 mol %. The lamp intensity was 13 mW/cm$^2$. In all cases, the oxetane monomers containing benzyl moieties were observed to be more reactive and to require smaller irradiation doses to reach the same % conversion to polymer than did monomer 2.

TABLE 6

| Monomer # | irradiation dose in mJ/cm$^2$ for the following conversions | | | |
|---|---|---|---|---|
| | 50% | 60% | 70% | 75% |
| 2 | 400 | 600 | 1000 | 1500 |
| 14 | 200 | 250 | 500 | 1000 |
| 17 | 65 | 75 | 85 | 75 |
| 18 | 85 | 95 | 110 | 120 |
| 19 | 40 | 45 | 55 | 60 |

We claim:

1. A compound of formula $$\left[ \begin{array}{c} O \\ \diamond\!\!\!\diamond \\ R^1 \end{array} \!\!\! Z\!\!-\!\!R^2 \right]_m$$

wherein R$^1$ is alkyl of 1 to 6 carbons;
R$^2$ is $$-(CH_2)_3-\underset{\underset{R^4}{|}}{\overset{\overset{R^4}{|}}{Si}}-O\!-\!\!\left(\underset{\underset{R^3}{|}}{\overset{\overset{R^3}{|}}{Si}}-O\right)_{\!\!n}\!\!\underset{\underset{R^4}{|}}{\overset{\overset{R^4}{|}}{Si}}-(CH_2)_3-$$

R$^3$ is chosen from the group consisting of alkyl of 1–4 carbons and $$-O\!-\!\!\left(\underset{\underset{R^5}{|}}{\overset{\overset{R^5}{|}}{Si}}-O\right)_{\!\!j}\!\!\underset{\underset{R^5}{|}}{\overset{\overset{R^5}{|}}{Si}}-(CH_2)_3-,$$

R$^4$ is alkyl of 1 to 4 carbons;
R$^5$ is alkyl of 1 to 4 carbons;
Z is oxygen or sulfur;
j is zero or an integer from 1 to 100;
m is 3, 3 or 4; and
n is an integer from zero to 2000.

2. A compound according to claim 1 wherein R$^3$ is alkyl and m is two.

3. A compound according to claim 2 wherein R$^3$ is methyl and n is from zero to 6.

4. A compound according to claim 2 wherein R$^3$ is methyl and n is from 100 to 200.

5. A compound having the formula $$\left[ \begin{array}{c} O \\ \diamond\!\!\!\diamond \\ R^1 \end{array} \!\!\! O\!\!-\!\!\underset{\underset{R^4}{|}}{\overset{\overset{R^4}{|}}{Si}}\!\!-\!\!O\!- \right]_{\!\!4}\!\!Si$$

wherein

R$^1$ is hydrogen, alkyl of 1 to 6 carbons, fluorine, fluoroalkyl of 1 to 6 carbons, allyl, aryl, furan or thiophene; and R$^4$ is alkyl of 1 to 4 carbons.

6. A compound according to claim 5 wherein R$^1$ is ethyl and R$^4$ is methyl.

7. A compound of formula $$R^{11}\!-\!O\!\!\left[\!\!\underset{\underset{(CH_2)_3}{|}}{\overset{\overset{R^5}{|}}{Si}}\!-\!O\!\right]_{\!\!r}\!\!R^{11}$$

wherein R$^1$ is hydrogen, alkyl of 1 to 6 carbons, fluorine, fluoroalkyl of 1 to 6 carbons, allyl, aryl, furan or thiopene;

R$^5$ is alkyl of 1 to 4 carbons;

R$^{11}$ is alkyl of 1 to 4 carbons or trialkylsilyl; and r is an integer from 25 to 200.

* * * * *

UNITED STATES PATENT AND TRADEMARK OFFICE
CERTIFICATE OF CORRECTION

PATENT NO. : 5,463,084
DATED : Oct. 31, 1995
INVENTOR(S) : Crivello et al.

It is certified that error appears in the above-indentified patent and that said Letters Patent is hereby corrected as shown below:

Column 18, line 2, delete 3, 3 or 4; and insert therefor --2, 3, or 4--.

Column 18, line 48, delete thiopene and insert therefor --thiophene".

Signed and Sealed this

Fifth Day of March, 1996

*Attest:*

BRUCE LEHMAN

*Attesting Officer*  *Commissioner of Patents and Trademarks*